United States Patent
Seidel et al.

(10) Patent No.: US 6,447,992 B1
(45) Date of Patent: *Sep. 10, 2002

(54) METHOD FOR SEROLOGICAL TYPING USING TYPE-SPECIFIC ANTIGENS

(75) Inventors: Cristoph Seidel, Weilheim; Ursula-Henrike Wienhues-Thelen, Krailling; Urban Schmitt, Oberhausen; Günther-Gerhard Jung, Tübingen; Hans-Georg Ihlenfeldt, Tübingen; Wolfgang Kraas, Tübingen, all of (DE)

(73) Assignee: Roche Diagnostics Gmbh, Mannheim (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/351,296

(22) Filed: Jul. 12, 1999

Related U.S. Application Data

(62) Division of application No. 08/845,926, filed on Apr. 28, 1997, now Pat. No. 5,935,778, which is a continuation of application No. 08/598,993, filed on Feb. 9, 1996, now abandoned.

(30) Foreign Application Priority Data

Feb. 9, 1995 (DE) .......................................... 195 04 302

(51) Int. Cl.⁷ ........................... A61K 39/29; C12Q 1/70
(52) U.S. Cl. ........................... 435/5; 435/7.1; 530/300; 530/350; 424/189.1; 424/204.1; 424/228.1
(58) Field of Search ................... 435/5, 7.1; 530/300, 530/350; 424/189.1, 204.1, 228.1

(56) References Cited

U.S. PATENT DOCUMENTS

| | | | | |
|---|---|---|---|---|
| 4,315,907 A | * | 2/1982 | Fridlender et al. ........... | 424/1 |
| 4,539,292 A | * | 9/1985 | Reid et al. ................... | 435/7.1 |
| 5,428,145 A | * | 6/1995 | Okamoto et al. ........... | 536/23.72 |
| 5,582,968 A | * | 12/1996 | Wang et al. ................. | 435/5 |
| 5,847,101 A | * | 12/1998 | Okayama et al. ........... | 536/23.72 |
| 5,891,640 A | * | 4/1999 | De Leys ..................... | 435/7.1 |
| 5,935,778 A | * | 8/1999 | Seidel et al. ................. | 435/5 |

FOREIGN PATENT DOCUMENTS

| | | | |
|---|---|---|---|
| EP | 0 435 229 | * | 7/1991 |
| EP | 0 445 423 A2 | * | 9/1991 |
| JP | 04179482 | * | 6/1992 |
| JP | 05176774 | * | 7/1993 |
| JP | 06102273 | * | 4/1994 |
| WO | WO93/06247 | * | 4/1993 |
| WO | WO93/18054 | * | 9/1993 |
| WO | WO-93/18054 | * | 9/1993 |
| WO | WO94/27153 | * | 11/1994 |

OTHER PUBLICATIONS

Inchauspe et al. (1991 PNAS USA vol. 88 pp. 10292–10296).*
Okamoto et al. (1991 Journal of General Virology vol. 72 pp. 2697–2704).*
Okamoto et al. (1992 Virology vol. 88 pp. 331–341).*
Greene et al. (1995 Journal of General Virology vol. 76 Pt 1 (Jan.) pp. 211–215).*
Harlow et al., "Immunoassays" In: Antibodies A Laboratory Manual, Cold Spring Harbor Lab, New York, p. 553–612 (1988).*
Harlow et al., "Immunoassays" In: Antibodies a Laboratory Manual, Cold Spring Harbor Lab, New York, p. 313–315 (1988).*
Zhang, et al. Journal of Medical Virology 45:50–55 (1995) "Evaluation of a Multiple Peptide Assay for Typing of Antibodies to the hepatitis C Virus: relation to Genomic Typing by the Polymerase Chain Reaction".*

* cited by examiner

*Primary Examiner*—Mary K. Zeman
(74) *Attorney, Agent, or Firm*—Arent Fox Kintner Plotkin & Kahn

(57) ABSTRACT

The invention concerns a method for typing antibodies in a sample liquid by means of type-specific antigens and in particular a method for typing antibodies to the hepatitis C virus and peptide antigens suitable for this.

18 Claims, 1 Drawing Sheet

METHOD FOR SEROLOGICAL TYPING USING TYPE-SPECIFIC ANTIGENS

Figure 1:
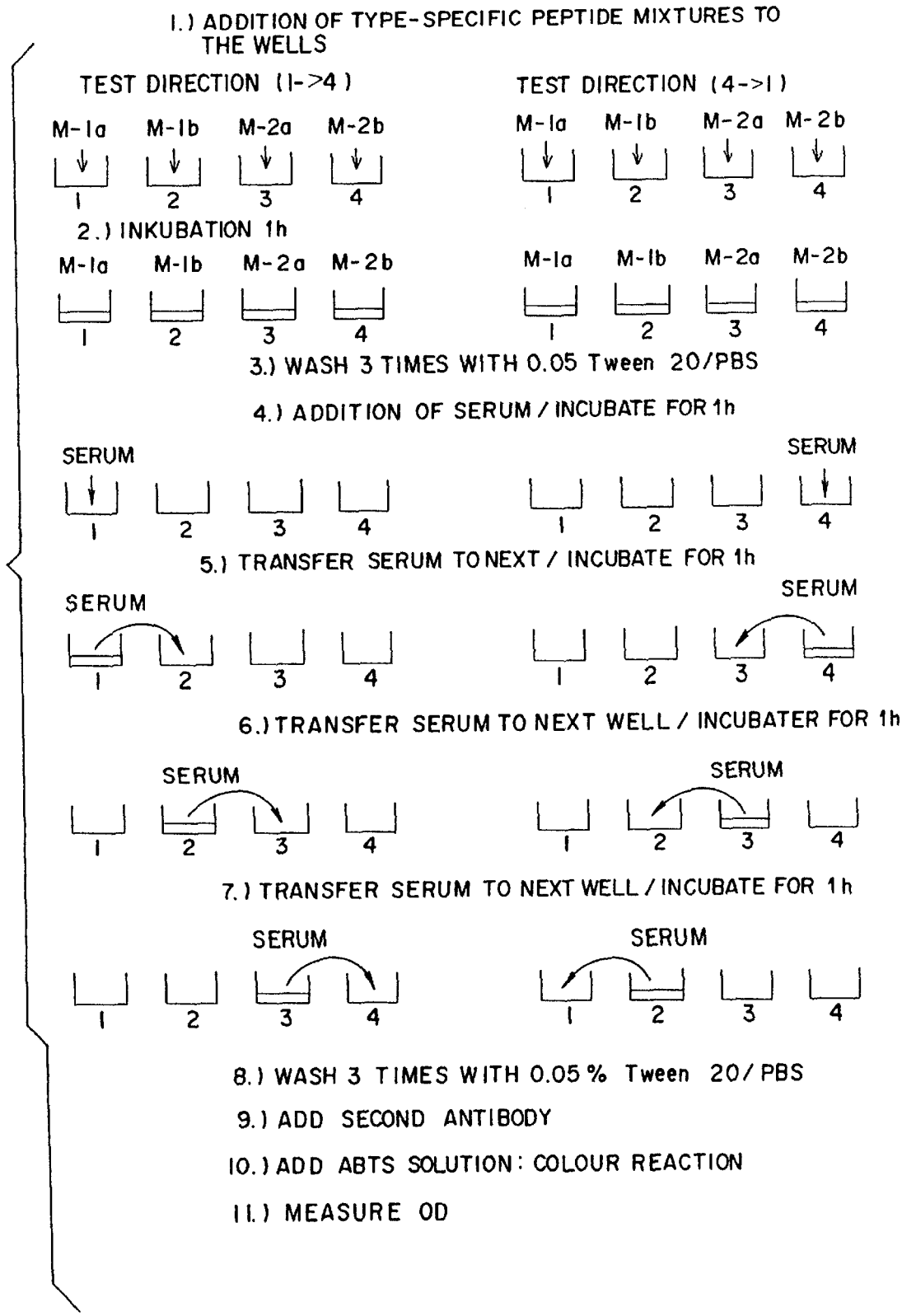

This application is a divisional application of U.S. Ser. No. 08/845,926, filed Apr. 28, 1997 now U.S. Pat. No. 5,935,778, which is a continuation application of U.S. Ser. No. 08/598,993, filed Feb. 9, 1996, now abandoned.

DESCRIPTION

The invention concerns a method for typing antibodies in a sample liquid using type-specific antigens, and in particular a method for typing antibodies to hepatitis C virus and peptide antigens that are suitable for this.

The disease referred to as non-A-non-B hepatitis is in many cases caused by the hepatitis C virus (HCV). HCV is a single-stranded encapsulated RNA virus the genome of which is composed of about 9000 to 10000 bases. Structural proteins (core and envelope proteins) and non-structural proteins are coded by this genome.

HCV is a virus that is of major clinical importance since it correlates with chronic infections and diseases which occur later in infected patients such as cryptic cirrhosis and primary carcinoma of the liver.

HCV can be transmitted by blood contact. Investigations on the occurrence of antibodies indicate that it is highly contagious.

EP-A-0 318 216 discloses a partial nucleotide sequence of a HCV. EP-A-0 450 931 discloses the complete nucleotide and amino acid sequence of a HCV. Methods are known for the diagnostic detection of a HCV infection by determining viral antibodies in body fluids using viral proteins or peptides as antigens (cf. for example Mori et al., Jpn. J. Cancer Res. 83 (1992), 264–268; WO92/11370 and DE-A-44 28 705.4).

The problem with a HCV infection is that there are different virus strains which have a considerable variability in their genome and accordingly in the polypeptides coded by this genome (cf. for example McOmish et al, Bioforum 16 (1993), 414–420.

Due to the variability of HCV it is on the one hand difficult to diagnose an infection at all and on the other hand to type the virus strain responsible for the infection. Such typing is important since there are significant differences in the virulence and response to therapy (e.g. with interferon) of the various virus strains.

One way of typing virus strains is to determine the genotype by amplifying the viral genome by means of PCR and subsequently determining the sequence (e.g. Bukh et al., Proc. Natl. Acad. Sci. USA 90 (1993), 8234–8238). A disadvantage of this determination of the genotype is, however, that the amplification and sequence determination steps are very time-consuming and can only be carried out using complicated apparatuses in laboratories that are specially equipped for this. This is all the more so in this case since there is often only an extremely small amount of viral genetic material that can be amplified in a HCV infection.

A further possibility of type determination is serotyping i.e. determination of the virus type by means of the immunological specificity of the antibody to the virus produced in the organism. Simmonds et al. (J. Clin. Microbiol. 31 (1993), 1493–1503) describe the use of type-specific peptide antigens for the serological differentiation of infections with the HCV types 1, 2 and 3. The typing was carried out by means of an indirect ELISA using peptide antigens of the amino acid regions 1691–1708 and 1710–1728 from the NS4 region of HCV. For this type-specific peptide antigens were each immobilized separately according to their type in individual wells of a microtitre plate and each was contacted with separate aliquots of a plasma sample from HCV-infected blood donors. The typing was carried out according to the reactivity of the serum sample with the individual peptide antigens. However, this method is relatively inaccurate and, moreover, does not allow the determination of individual viral subtypes i.e. individual virus strains whose immunogenicity only differs to a slight extent.

The object of the present invention was therefore to provide a new method for typing antibodies which on the one hand can be carried out routinely and without elaborate apparatus and which on the other hand enables classification between individual antibody types that is sufficiently accurate. A further object of the present invention was to identify regions from the genome of HCV which at the same time have a high immunogenicity and variability so as to be suitable for typing HCV infections.

This object is achieved by a fractional immunosorption method in which a first aliquot of a sample liquid which contains the antibodies to be typed is contacted successively with a series of type-specific antigens or antigen mixtures and optionally a second aliquot or further aliquots of the sample liquid are likewise contacted with various type-specific antigens or antigen mixtures but each time in another sequence. Furthermore new immunogenic peptide sequences from the HCV genome are provided which enable a better typing than the sequences known from the state of the art.

A first aspect of the present invention is a method for typing antibodies in a sample liquid which is characterized in that (a) a first aliquot of the sample liquid is contacted with a first immobilized antigen which is specific for a first type of the antibodies to be examined or with a first mixture of immobilized antigens each of which is specific for a first type of the antibodies to be examined under conditions in which the antigen or antigen mixture can react with the antibodies and in which the amount of antibody in the sample liquid does not exceed the capacity of the immobilized antigen or antigen mixture, (b) the sample liquid from step (a) is contacted with a second immobilized antigen which is specific for a second type of antibodies to be examined or with a mixture of immobilized antigens each of which is specific for a second type of antibodies to be examined under conditions as in step (a), the second antigen or antigen mixture being spatially separate from the first antigen or antigen mixture used in step (a), (c) the measures according to step (b) are optionally repeated with one or several further antigens or antigen mixtures which are specific for one or several further types of antibodies to be examined, the further antigens or antigen mixtures each being spatially separate from the antigens or antigen mixtures used in the previous steps, (d) a second aliquot of the sample liquid is optionally contacted with several immobilized antigens or antigen mixtures according to steps (a) to (c) in which the sequence of antigens or antigen mixtures is, however, different, (e) the respective immunological reactivity of the immobilized antigens or antigen mixtures with the sample liquid is determined qualitatively or/and quantitatively and (f) a typing of the antibodies present in the sample liquid is carried out based on the reactivity determination.

Any antibodies can be examined as typing objects e.g. antibodies which are directed towards pathogens or autoimmune antigens. Antibody typing in turn enables a typing of the antigens to which the organism was exposed and which have caused the formation of antibodies. It is preferable to type antibodies that are directed towards one or several pathogens, especially antibodies that are directed towards viral antigens. Examples of viruses from which viral antigens are derived are HCV, human papilloma virus (HPV), hepatitis B virus (HBV) and HIV. The method can also be used for the concurrent detection of several viral infections which are present together e.g. HCV and HIV.

The application of the method according to the invention is of particular importance for typing a HCV infection since the virulence and response to interferon therapy differs among the individual virus types and subtypes. However, the method can also be used advantageously for other viruses such as HIV in order to determine the origin of individual viral isolates or to identify subtypes (e.g. subtype O in the case of HIV).

In the method according to the invention an aliquot of sample liquid, e.g. a body fluid which is optionally diluted such as blood, plasma, serum or urine, is contacted successively with several immobilized type-specific antigens or antigen mixtures in order to enable a stepwise sorption of the antibodies capable of reacting with the respective antigens or antigen mixtures and thus to enable their stepwise removal from the sample liquid. Preferably one or several further aliquots of the sample liquid are contacted concurrently with the immobilized antigens or antigen mixtures in a sequence which is different to that of the first aliquot. If two aliquots of the sample liquid are used, the second aliquot is preferably contacted with the immobilized antigens or antigen mixtures in the reverse order to that of the first aliquot.

In order to achieve sorption of one type of antibodies to the respective antigen which is as quantitative as possible, the amount of antibody in the sample liquid should not exceed the capacity of the immobilized antigens. This can be achieved in a simple manner by appropriate dilutions of the sample liquid. Due to the consecutive sorption steps using several different type-specific immobilized antigens or antigen mixtures, the method according to the invention is a fractional immunosorption.

Type-specific antigen mixtures are preferably used for the individual sorption steps of the method according to the invention. Type-specific antigen mixtures are mixtures of antigens which are derived from the same regions of individual variants within one type of antigen to be classified and which have only slight differences between one another compared with other antibody types to be classified, or/and mixtures of antigens which are derived from different regions of the same antigen type.

The immobilized type-specific antigens with which the sample liquid is contacted may be any antigens provided that they enable a typing of the antibodies which are capable of reacting therewith. The antigens are preferably peptide sequences containing an immunologically active region of at least 6 amino acids. An immunologically active region preferably has a length of 30 amino acids at most and particularly preferably a length of 9 to 20 amino acids.

In addition to an immunologically active region, the peptide can preferably also contain a spacer region which can for example be used to couple it to other immunologically active regions or to a carrier or/and to couple marker groups or solid phase binding groups.

The spacer region is preferably an immunologically inactive peptide sequence with a length of 1 to 10 amino acids. The amino acids of the spacer region are preferably selected from natural or artificial amino acids, in particular from amino acids of the group comprising glycine, β-alanine, γ-amino butyric acid, ε-aminocaproic acid and lysine. The spacer region is preferably a continuous sequence of amino acids at the amino or/and carboxy terminus of the immunologically active epitope region.

The immobilized antigens may be bound to any solid phases e.g. to the wall or/and the bottom of a reaction vessel, to columns or also to particulate solid phases. Antigens immobilized on microtitre plates are particularly preferably used.

The immobilization of the antigens on the solid phase can be carried out in any arbitrary manner. In a preferred embodiment of the method according to the invention the antigens carry a solid phase binding group via which they are coupled to a reactive solid phase by means of an affinity interaction. The solid phase binding group is preferably selected from biotin or biotin derivatives such as iminobiotin or desthiobiotin which can bind to a solid phase coated with streptavidin or avidin. Other examples of suitable solid phase binding groups are haptens such as dinitrophenol, digoxin, digoxigenin etc., which can bind to a solid phase coated with a hapten-specific antibody.

On the other hand the antigens can also be linked covalently to the solid phase e.g. via a bifunctional spacer. Finally the antigens may also be present conjugated to a carrier which is adsorptively coupled to the solid phase. Examples of suitable carriers are protein molecules such as bovine serum albumin. Other immobilization methods for antigens and in particular for peptide antigens on a solid phase are known to a person skilled in the art and therefore do not need to be elucidated in more detail.

The qualitative or/and quantitative determination of the reactivity of antibodies present in the sample with the immobilized antigens can be carried out in any known manner e.g. by incubation with a labelled second antibody which can species-specifically recognize an antibody from the sample liquid (e.g. a goat anti-human antibody). The antibodies are typed based on the reactivity determinations. If it is intended to type antibodies which are directed towards very similar antigens (e.g. viral subtypes), it is preferable to contact a further aliquot of the sample liquid with the antigens or antigen mixtures to be immobilized in a different sequence than that of the first aliquot (step (d) of the method according to the invention). If the same subtype then results in both test directions, an unequivocal differentiation can be achieved.

The method according to the invention of fractional immunosorption enables a considerable saving of time, saving of sample material, reaction vessels, antigens and incubation buffer compared to state of the art methods in which a preincubation of different sera with peptides of heterologous types is carried out in separate ELISA plates that are not coated with streptavidin. In addition the new method combines the advantage of a duplicate determination with that of a preincubation of the sample material without using up additional sample material in this process.

The method according to the invention is particularly suitable for typing antibodies to hepatitis C virus (HCV). Antigens are required for this typing which fulfill two prerequisites namely an immunogenic action i.e. the ability to cause the formation of antibodies which are directed towards these sequences and in addition a variability in individual virus types or subtypes which is the basis for being able to differentiate the individual virus isolates.

Surprisingly peptide sequences were identified from the genome of HCV which fulfill these two requirements extremely well. These peptide sequences are suitable for the production of peptide antigens for a method for determining antibodies to hepatitis C virus.

Therefore a further subject matter of the present invention is a peptide comprising at least one immunologically active region from the hepatitis C virus which is selected from
  (a) the amino acids 384–414,
  (b) the amino acids 1738–1759,
  (c) the amino acids 2217–2236,
  (d) the amino acids 2402–2419,
  (e) the amino acids 2345–2357
and partial sequences thereof which have a length of at least six amino acids in which the numbering of the amino acid residues relates to FIG. 1 of EP-A-0 450 931.

The peptide according to the invention can be derived from any HCV isolate such as from a HCV isolate with the nucleotide sequence described in EP-A-0 450 931.

If the peptide is derived from the region of amino acids 384–414 which is located in the hypervariable region, the immunologically active region is preferably selected from (a) the amino acid sequences shown in SEQ ID NO. 1 to 10, (b) amino acid sequences which have a homology of at least 90% to one of the sequences from (a), or (c) partial sequences of the sequences from (a) or (b) with a length of at least 6 amino acids.

The term "homology" is understood within the sense of the present application as a percentage value which results when one divides the number of identical amino acids of two amino acid sequences which are to be compared by the number of all the amino acids of one of the two sequences.

The sequence protocols SEQ ID NO. 1 to 3 show HCV sequences from the hypervariable region of virus isolates of type 1a. SEQ ID NO. 4 to 6 show sequences of virus isolates of type 1b. SEQ ID NO. 7 shows a sequence of a virus isolate of type 2a. SEQ ID No. 8 and 9 show sequences of virus isolates of type 2b. SEQ ID NO. 1 to 10 show the sequence of a virus isolate obtained from Taiwan.

In addition the immunologically active region of the peptide can be selected from the amino acids 1738–1759 of the NS4 region and in particular from the amino acid sequences shown in SEQ ID NO. 11 to 16, (b) amino acid sequences which have a homology of at least 90% to one of the sequences from (a), or (c) partial sequences of the sequences from (a) or (b) with a length of at least 6 amino acids. SEQ ID NO. 11 and 12 show sequences of virus isolates of type 1a. SEQ ID NO. 13 shows a sequence of a virus isolate of type 1b. SEQ ID NO. 14 shows a sequence of a virus isolate of type 2a. SEQ ID NO. 15 shows a sequence of a virus isolate of type 2b. SEQ ID NO. 16 shows a sequence of a virus isolate obtained from Taiwan.

If the peptide is derived from the region of amino acids 2217–2236 of the NS5 region, its immunologically active region is preferably selected from (a) the amino acid sequences shown in SEQ ID NO. 17 to 22, (b) amino acid sequences which have a homology of at least 90% to one of the sequences from (a), or (c) partial sequences of the sequences from (a) or (b) with a length of at least 6 amino acids. SEQ ID NO. 17 shows the sequence of a virus isolate of type 1a. SEQ ID NO. 18 and 19 show sequences of virus isolates of type 1b. SEQ ID NO. 20 shows the sequence of a virus isolate of type 2a. SEQ ID NO. 21 shows the sequence of a virus isolate of type 2b. SEQ ID NO. 22 shows the sequence of a virus isolate obtained from Taiwan.

If the peptide is derived from amino acids 2402–2419 of the NS5 region, its immunologically active region is preferably selected from (a) the amino acid sequences shown in SEQ ID NO. 23 to 24, (b) amino acid sequences which have a homology of at least 90% to one of the sequences from (a), or (c) partial sequences of the sequences from (a) or (b) with a length of at least 6 amino acids. SEQ ID NO. 23 to 24 show sequences of virus isolates of types 2a and 2b.

If the peptide is derived from amino acids 2345–2357 of the NS5 region, the immunologically active region is preferably selected from (a) the amino acid sequences shown in SEQ ID NO. 25 to 30, (b) amino acid sequences which have a homology of at least 90% to one of the sequences from (a), or (c) partial sequences of the sequences from (a) or (b) with a length of at least 6 amino acids. SEQ ID NO. 25 and 26 show sequences of virus isolates of type 1a. SEQ ID NO. 27 shows a sequence of a virus isolate of type 1b. SEQ ID NO. 28 and 29 show sequences of virus isolates of types 2a and 2b. SEQ ID NO. 30 shows the sequence of a virus isolate obtained from Taiwan.

The immunologically active region of the peptides preferably has a length of 30 amino acids at most, particularly preferably of 9 to 20 amino acids. The peptide can also comprise an immunologically inactive spacer region as defined above in addition to the immunologically active HCV peptide region.

In addition the peptide according to the invention can carry at least one solid phase binding group which is preferably selected from biotin and biotin derivatives. However, the peptide may also carry a marker group. The marker group may be any radioactive or non-radioactive marker group. The preferred non-radioactive marker groups may be directly or/and indirectly detectable. In the case of a directly detectable label the group generating a detectable measuring signal is located directly on the peptide antigen. Examples of such direct signal-generating groups are chromogens (fluorescent or luminescent groups, dyes), enzymes, NMR-active groups or metal particles, which are coupled in a known manner to a peptide antigen. The directly detectable marker group is preferably a metal complex that can be directly detected by electrochemiluminescence and particularly preferably a ruthenium complex. Suitable metal complexes are described for example in EP-A-0 580 979, WO90/05301, WO90/11511 and WO92/14138. Reference is hereby made to these documents.

Another type of label is the indirectly detectable label. In this type of label the peptide antigen is coupled to an indirectly detectable group e.g. a hapten group which in turn can be detected by reaction with a suitable binding partner (e.g. anti-hapten antibody) which in turn carries a signal-generating group.

The new peptides described above can be used in a method for the determination of antibodies to hepatitis C virus. On the one hand they can be used as antigens in a diagnostic method for detecting a HCV infection e.g. in a double antigen bridge test in which a sample liquid is incubated with at least two peptides P1 and P2 wherein the peptide P1 (a) is bound to a solid phase or (b) is present in a form capable of binding to a solid phase and the peptide P2 carries a marker group. The antibody in the sample liquid is detected by determining the label in the solid phase or/and in the liquid phase, preferably in the solid phase, by means of an immobilized immunocomplex. Peptide mixtures of various types or subtypes of HCV are preferably used as antigens in such a method for detecting a HCV infection so that a HCV infection can be unequivocally detected independent of its type or subtype.

On the other hand the peptides according to the invention can also be used in a method for typing antibodies to HCV in which the typing procedure is preferably carried out by the method of fractional immunosorption.

In this connection it should be noted that the typing of HCV antibodies by the method of fractional immunosorption can not only be carried out using the above-mentioned peptides but that peptides from other sequence regions of the HCV genome are also suitable e.g. the peptides stated in example 2 or partial sequences thereof with a length of at least 6 amino acids.

It is intended to further elucidate the method according to the invention by the following examples, figures and sequence protocols.

FIG. 1 shows a diagram for carrying out typing by the method of fractional immunosorption.

SEQ ID NO. 1 to 10 show amino acid sequences of various hepatitis C virus isolates in the region of the amino acids 384–414

SEQ ID NO. 11 to 16 show amino acid sequences of various hepatitis C virus isolates in the region of the amino acids 1738–1759

SEQ ID NO. 17 to 22 show amino acid sequences of various hepatitis C virus isolates in the region of the amino acid sequences 2217–2236

SEQ ID NO. 23 to 24 show amino acid sequences of various hepatitis C virus isolates from the amino acid sequences 2402–2419 and SEQ ID NO. 25 to 30 show amino acid sequences of various hepatitis C virus isolates from the region of the amino acids 2345–2357.

EXAMPLE 1

Synthesis of Biotin Peptide Amides from Five Different Regions of the HCV Polyprotein and Their Use for Typing HCV Sera The synthesized partial regions were selected in such a manner that they are distinguished by a slight sequence homology between isolates of types 1a, 1b, 2a, 2b and Taiwan (belongs to 1b) of the respective region by which means the synthesized peptides can be used for serological typing corresponding to the respective HCV types. In addition type-overlapping synthesis of appropriate regions enables possible recognition gaps in HCV diagnostics to be closed by testing peptides that do not belong to the HCV-1 isolate according to EP-A-0 450 931 which has previously always served as the basis.

The hypervariable region which partially has a high degree of amino acid substitution as well as regions in which an insertion or deletion is made in the sequence of certain HCV isolates compared to other isolates are selected as special regions.

Test Instructions 24 sera were tested wherein the ELISA test was carried out as follows:

1.) coat a streptavidin ELISA plate with 100 µl peptide solution (concentration 50 ng/100 µl), 1 h
2.) wash three times with 0.05% Tween 20/PBS
3.) incubate with 100 µl serum (diluted 1:100), 1 h
4.) wash three times with 0.05% Tween 20/PBS
5.) incubate with 150 µl of a labelled second antibody (goat anti-human antibody-peroxidase conjugate, diluted 1:10000), 1 h
6.) ABTS® colour reaction, 1 h
7.) measure OD (positive HCV detection above 200 mOD)

The following biotin peptide amides from different regions of the HCV polyprotein were tested against 24 sera.

1. E2/NS1 region (hypervariable region) [AA 384–414]: peptides according to SEQ ID NO. 1–10
2. NS4 region [AA 1738–1759]: peptides according to SEQ ID NO. 11–16
3. NS5 region [AA 2217–2236, deletion]: peptides according to SEQ ID NO. 17–22
4. NS5 region [AA 2402–2419, insertion]: peptides according to SEQ ID NO. 23–24
5. NS5 region [AA 2345–2357, deletion]: peptides according to SEQ ID NO. 25–30

Result:

The tested peptides (SEQ ID NO. 1–30) proved to be suitable for typing HCV-positive sera. The peptides from the hypervariable region were especially superior to peptides known from the state of the art (Simmonds et al., J. Clin. Microbiol. 31 (1993), 1493–1503).

EXAMPLE 2

Serological Typing of HCV Sera Using the Method of Fractional Immunosorption

A new method based on a fractional immunosorption was developed for typing HCV sera.

Typing was carried out using peptide mixtures which only contained subtype-specific biotin peptide amides:

M-1a: only contains peptides of type 1a
M-1b: only contains peptides of type 1b
M-2a; only contains peptides of type 2a
M-2b: only contains peptides of type 2b.

The test procedure is shown diagrammatically in FIG. 1. Test in the direction [1→4]:

1.) Coat 4 wells of a streptavidin-coated microtitre plate with in each case 100 µl of the subtype-specific peptide mixtures M-1a (well 1), M-1b (well 2), M-2a (well 3) and M-2b (well 4), 1 h.
2.) wash three times with 0.05% Tween 20/PBS
3.) add 100 µl of the serum diluted 1:100 to well 1, incubate for 1 h
4.) quantitatively transfer 100 µl serum from well 1 to well 2, incubate for 1 h
5.) quantitatively transfer 100 µl serum from well 2 to well 3, incubate for 1 h
6.) quantitatively transfer 100 µl serum from well 3 to well 4, incubate for 1 h
7.) wash all 4 wells three times with 0.05% Tween 20/PBS
8.) add 150 µl second antibody (goat anti-human-POD conjugate, dilution 1:10000) to all 4 wells, incubate for 1 h
9.) wash three times with 0.05% Tween 20/PBS
10.) colour reaction: add 150 µl ABTS® solution, incubate for 1 h
11.) measure OD With regard to preincubation of the serum the following can be established:

When the serum reaches well 4 (peptide mixture M-2b) i.e. test of the serum for type 2b, it has been maximally preincubated by peptides of types 1a (well 1), 1b (well 2) and 2a (well 3). The preincubation of the serum is correspondingly less when it is tested for type 2a (preincubation by peptides of types 1a and 1b) and for type 1b (preincubation by peptides of type 1a). Thus the serum is not subjected to a type-heterologous preincubation when measuring the OD in well 1 (test of the serum for type 1a).

In order to avoid the sequence of the serum transfer (well 1→2→3→4) i.e. the degree of preincubation, having an influence on test results, the serum transfer technique is additionally carried out in the reverse order (well 4→3→2→1). The test [4→1] is carried out concurrently with the above-mentioned test [1→4].

The procedure is as in sequence [1→4] except that the serum sample is firstly added to well 4, then to well 3, then to well 2 and finally to well 1.

With respect to preincubation of the serum the following can be similarly established:

When the serum reaches well 1 (peptide mixture M-1a) i.e. test of the serum for type 1a, it has been maximally preincubated by peptides of types 2b (well 4), 2a (well 3) and 1b (well 2). The preincubation of the serum is correspondingly less when it is tested for type 1b (preincubation by peptides of types 2b and 2a) and for type 2a (preincubation by peptides of type 2b). Thus the serum is not subjected to a type-heterologous preincubation when measuring the OD in well 4 (test of the serum for type 2b).

Biotin Peptide Amides Used:
Core 4 region:
A (HCV-1): biotin-PIPKA RRPEG RTWAQ PGY-NH$_2$ (SEQ ID NO:31) type 1 (a+b) MW: 2689.19 g/mol;
B (HCV-J6): biotin-PIPKD RRSTG KSWGK PGY-NH$_2$ (SEQ ID NO:32) type 2 (a+b) MW: 2639.13 g/mol;
E1 region:
C (HCV-1): biotin-ATRDGKLPATQLRRHIDLLKG-NH$_2$ (SEQ ID NO:33) type 1a MW: 2968.57 g/mol;
D (HCV-J): biotin-AARNSSIPTTTIRRHVDLLVG-NH$_2$ (SEQ ID NO:34) type 1b MW: 2886.41 g/mol;
E (HCV-J6): biotin-AVQQPGALTQGLRTHIDMVVM-NH$_2$ (SEQ ID NO:35) type 2a MW: 2874.49 g/mol;
F (HCV-J7/J8): biotin-AVKHRGALTRSLRTHVDMIVM-NH$_2$ (SEQ ID NO:36) type 2b MW: 3001.71 g/mol;
NS 4/1 region:
G (HCV-1): biotin-S Q H L P Y I E Q-NH$_2$ (SEQ ID NO:37) type 1a MW: 1723.02 g/mol;
H (HCV-J): biotin-A S H L P Y I E Q-NH$_2$ (SEQ ID NO:38) type 1b MW: 1664.86 g/mol;
I (HCV-J6): biotin-A S R A A L I E E-NH$_2$ (SEQ ID NO:39) type 2a MW:
J (HCV-J8): biotin-A S K A A L I E E-NH$_2$ (SEQ ID NO:40) type 2b MW: 1538.84 g/mol;
NS 4/2 region:
K (HCV-1): biotin-QKALGLLQT-NH$_2$ (SEQ ID NO:41) type 1a MW: 1578.92 g/mol;
L (HCV-J); biotin-SKIQGLLQQ-NH$_2$ (SEQ ID NO:42) type 1b MW: 1621.93 g/mol;
NS 5/1 region:
M (HCV-1): biotin-SRRFAQALPVWARPD-NH$_2$ (SEQ ID NO:43) type 1a MW: 2378.83 g/mol;
N (HCV-J): biotin-PRKFPPALPIWARPD-NH$_2$ (SEQ ID NO:44) type 1b MW: 2369.90 g/mol;
O (HCV-J6): biotin-KKRFPPALPAWARPD-NH$_2$ (SEQ ID NO:45) type 2a MW: 2358.89 g/mol;
P (HCV-J8): biotin-RRKFPPALPPWARPD-NH$_2$ (SEQ ID NO:46) type 2b MW: 2412.94 g/mol;
Peptide Mixtures:
M-1a: 100 µl M-1a composed of 20 µl of each of the peptides A, C, G, K and M (concentration: 2.5 µg/ml, i.e. 50 ng/20 µl).

[4 ml of the mixture M-1a composed of 400 µl of a peptide solution of each of the above-mentioned 5 peptides (concentration; 5 µg/ml)+2 ml buffer]

M-1b: 100 µl M-1b composed of 20 µl of each of the peptides A, D, H, L and N (concentration: 2.5 µg/ml, i.e. 50 ng/20 µl)

[4 ml of the mixture M-2b composed of 400 µl of a peptide solution of each of the above-mentioned 5 peptides (concentration: 5 µg/ml )+2 ml buffer]

M-2a: 100 µl M-2a composed of 25 µl of each of the peptides B, E, I and O (concentration: 2 µg/ml, i.e. 50 ng/25 µl)

[4 ml of the mixture M-2b composed of 400 µl of a peptide solution of each of the above-mentioned 4 peptides (concentration: 5 µg/ml)+2.4 ml buffer]

M-2b: composed of 25 µl of each of the peptides B, F, J and P (concentration: 2 µg/ml, i.e. 50 ng/25 µl)

[4 ml of the mixture M-2b composed of 400 µl of a peptide solution of each of the above-mentioned 4 peptides (concentration: 5 µg/ml)+2.4 ml buffer]

Result:

12 HCV-positive sera were typed using the fractional immunosorption method.

It was possible to type 11 of these 12 sera using the peptide panels while no reactivity was found in one serum (i.e. absorbance <200 mOD for all types) which allow typing even as a broad trend.

TABLE 2

Typing 11 HCV sera with peptide mixtures in both test directions in each case

| | Typing | | Result of |
|---|---|---|---|
| Sera | Test [1—>4] | Test [4—>1] | typing |
| 1 | type 1a | type 1a | type 1a |
| 2 | trend 1a | trend 1b | trend 1 |
| 3 | type 1a | type 1b | type 1 |
| 4 | type 1a | trend 1b | type 1 |
| 5 | type 1a | negative | type 1 |
| 6 | type 1a | type 1b | type 1 |
| 7 | type 1a | trend 2 | trend type 1 |
| 8 | type 1a | type 1b | type 1 |
| 9 | type 1a | type 1a | type 1a |
| 10 | type 1a | type 1b | type 1 |
| 11 | type 1a | trend 1b | type 1 |

When the reactivity was <200 mOD it was judged as a "trend . . . " if one type dominated or it was judged to be "negative" if the result was unclear.

Apart from making a statement about the type classification (i.e. type 1, 2 or 3) of the serum using the typing method carried out as above, the result shows that some sera (sera 1 and 9) can even be typed with regard to their subtype (1a, 1b, 2a, 2b). This is the case when both test directions i.e. test [1→4] and test [4→1] result in the same subtype.

What is claimed is:

1. A peptide suitable for detecting an antibody against hepatitis C virus, consisting of:
   (a) an isolated immunologically active amino acid sequence from the hepatitis C virus consisting of 6–22 amino acids from one of SEQ ID NOs: 12–16;
   (b) optionally, an immunologically inactive spacer region coupled to the immunologically active sequence; and
   (c) optionally, a solid phase binding group or a marker group coupled to the spacer region.

2. The peptide of claim 1, consisting of (a) and (b).

3. The peptide of claim 1, consisting of (a), (b) and (c).

4. The peptide of claim 1, wherein the immunologically active amino acid sequence consists of 9–20 amino acids from one of SEQ ID NOs: 12–16.

5. The peptide of claim 3, wherein (c) is a solid phase binding group.

6. The peptide of claim 5, wherein the peptide is bound to a solid phase via the solid phase binding group.

7. The peptide of claim 5, wherein the solid phase binding group is biotin or a biotin derivative.

8. The peptide of claim 3, wherein (c) is a marker group.

9. The peptide of claim 8, wherein the marker group is a luminescent metal complex or a fluorescent dye.

10. The peptide of claim 1, wherein the peptide is bound to a solid phase.

11. A method of detecting the presence or absence of an antibody against hepatitis C virus in a sample liquid, the method comprising the following steps:
    (a) incubating said sample liquid which may contain an antibody against hepatitis C virus with a peptide consisting of: (1) an isolated immunologically active amino acid sequence from the hepatitis C virus consisting of 6–22 amino acids from one of SEQ ID NOs: 12–16; (2) optionally, an immunologically inactive spacer region coupled to the immunologically active sequence; and (3) optionally, a solid phase binding group or a marker group coupled to the spacer region; and
    (b) detecting any binding between the antibody and the peptide, thereby detecting the presence or absence of the antibody in said sample liquid.

12. The method of claim 11, wherein the peptide consists of (1), (2) and (3).

13. The method of claim 12, wherein (3) is a solid phase binding group.

14. The method of claim 13, wherein the peptide is bound to a solid phase via the solid phase binding group.

15. The method of claim 11, wherein the immunologically active amino acid sequence consists of 9–20 amino acids from one of SEQ ID NOs: 12–16.

16. The method of claim 12, wherein (3) is a marker group.

17. A method of detecting the presence or absence of an antibody against hepatitis C virus in a sample, the method comprising the following steps:
    (a) incubating a first aliquot of the sample liquid with at least one first immobilized antigen which is specific for a first group of antibodies to be typed, to react the first group antibodies with the at least one first immobilized antigen, wherein the at least one first immobilized antigen consists of: (1) a first isolated immunologically active amino acid sequence from the hepatitis C virus consisting of 6–22 amino acids from one of SEQ ID NOs: 11–16; (2) an immunologically inactive spacer region coupled to the first immunologically active sequence; and (3) a solid phase binding group coupled to the spacer region, and the first group of antibodies is present in an amount which does not exceed the capacity of the at least one first immobilized antigen;
    (b) thereafter, separating the first aliquot from step (a) from the at least one first immobilized antigen, and incubating the first aliquot with at least one second immobilized antigen which is specific for a second group of antibodies to be typed, to react the second group of antibodies with the at least one second immobilized antigen, wherein the at least one second immobilized antigen consists of: (1) a second isolated immunologically active amino acid sequence from the hepatitis C virus consisting of 6–22 amino acids from one of SEQ ID NOs: 11–16, wherein the second immunologically active sequence is different than the first immunologically active sequence; (2) an immunologically inactive spacer region coupled to the second immunologically active sequence; and (3) a solid phase binding group coupled to the spacer region;
    (c) optionally repeating step (b) with at least one further antigen or antigens, each of which is specific for at least one further group of antibodies to be typed, wherein each of the at least one further antigen or antigens consists of: (1) a further isolated immunologically active amino acid sequence from the hepatitis C virus consisting of 6–22 amino acids from one of SEQ ID NOs: 11–16, wherein the further immunologically active sequence is different than the first immunologically active sequence and the second immunologically active sequence; (2) an immunologically inactive spacer region coupled to the second immunologically active sequence; and (3) a solid phase binding group coupled to the spacer region, and in each repeated step (b) the at least one further antigen or antigens are incubated separately from the antigen or antigens in a previous step (b);
    (d) optionally repeating steps (a) through (c) with a second aliquot of the sample liquid, wherein the sequence of antigens is different than for steps (a) through (c) conducted with the first aliquot;
    (e) qualitatively or quantitatively determining the immunological activity of the respective immobilized antigens with the respective groups of antibodies in the sample to be typed; and
    (f) typing the antibodies in the sample based on the determining step (e).

18. The method of claim 17, wherein each immunologically active amino acid sequence consists of 9–20 amino acids from one of SEQ ID NOs: 11–16.

* * * * *

SEQUENCE LISTING (1) GENERAL INFORMATION:

(iii) NUMBER OF SEQUENCES: 46

(2) INFORMATION FOR SEQ ID NO: 1:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 1:

```
Glu Thr His Val Thr Gly Gly Ser Ala Gly His Thr Val Ser Gly Phe
1               5                  10                  15

Val Ser Leu Leu Ala Pro Gly Ala Lys Gln Asn Val Gln Leu Ile
            20                  25                  30
```

(2) INFORMATION FOR SEQ ID NO: 2:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 2:

```
Glu Thr His Val Thr Gly Gly Asn Ala Gly Arg Thr Thr Ala Gly Leu
1               5                  10                  15

Val Gly Leu Leu Thr Pro Gly Ala Lys Gln Asn Ile Gln Leu Ile
            20                  25                  30
```

(2) INFORMATION FOR SEQ ID NO: 3:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 3:

```
His Thr Arg Val Thr Gly Gly Val Gln Gly His Val Thr Ser Thr Leu
1               5                  10                  15

Thr Ser Leu Phe Arg Pro Gly Ala Ser Gln Lys Ile Gln Leu Val
            20                  25                  30
```

(2) INFORMATION FOR SEQ ID NO: 4:

(i) SEQUENCE CHARACTERISTICS:
        (A) LENGTH: 31 amino acids
        (B) TYPE: amino acid (C) STRANDEDNESS:
            (D) TOPOLOGY: linear (ii) MOLECULE TYPE: peptide (vi) ORIGINAL SOURCE:
            (A) ORGANISM: Hepatitis C Virus (xi) SEQUENCE DESCRIPTION: SEQ ID NO: 4:

His Thr His Val Thr Gly Gly Arg Val Ala Ser Ser Thr Gln Ser Leu
1               5                   10                  15

Val Ser Trp Leu Ser Gln Gly Pro Ser Gln Lys Ile Gln Leu Val
                20                  25                  30

(2) INFORMATION FOR SEQ ID NO: 5:

(i) SEQUENCE CHARACTERISTICS:
            (A) LENGTH: 31 amino acids
            (B) TYPE: amino acid
            (C) STRANDEDNESS:
            (D) TOPOLOGY: linear (ii) MOLECULE TYPE: peptide (vi) ORIGINAL SOURCE:
            (A) ORGANISM: Hepatitis C Virus (xi) SEQUENCE DESCRIPTION: SEQ ID NO: 5:

Asp Thr His Val Thr Gly Gly Ala Gln Ala Lys Thr Thr Asn Arg Leu
1               5                   10                  15

Val Ser Met Phe Ala Ser Gly Pro Ser Gln Lys Ile Gln Leu Ile
                20                  25                  30

(2) INFORMATION FOR SEQ ID NO: 6:

(i) SEQUENCE CHARACTERISTICS:
            (A) LENGTH: 31 amino acids
            (B) TYPE: amino acid
            (C) STRANDEDNESS:
            (D) TOPOLOGY: linear (ii) MOLECULE TYPE: peptide (vi) ORIGINAL SOURCE:
            (A) ORGANISM: Hepatitis C Virus (xi) SEQUENCE DESCRIPTION: SEQ ID NO: 6:

Glu Thr His Val Thr Gly Gly Ser Ala Gly His Thr Val Ser Gly Phe
1               5                   10                  15

Val Ser Leu Leu Ala Pro Gly Ala Lys Gln Asn Val Gln Leu Ile
                20                  25                  30

(2) INFORMATION FOR SEQ ID NO: 7:

(i) SEQUENCE CHARACTERISTICS:
            (A) LENGTH: 31 amino acids
            (B) TYPE: amino acid
            (C) STRANDEDNESS:
            (D) TOPOLOGY: linear (ii) MOLECULE TYPE: peptide (vi) ORIGINAL SOURCE:
            (A) ORGANISM: Hepatitis C Virus (xi) SEQUENCE DESCRIPTION: SEQ ID NO: 7:

Gln Thr His Thr Val Gly Gly Ser Thr Ala His Asn Ala Arg Thr Leu
1               5                   10                  15

```
Thr Gly Met Phe Ser Leu Gly Ala Arg Gln Lys Ile Gln Leu Ile
            20                  25                  30
```

(2) INFORMATION FOR SEQ ID NO: 8:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 8:

```
Thr Thr Tyr Ser Ser Gly Gln Glu Ala Gly Arg Thr Val Ala Gly Phe
1               5                   10                  15
Ala Gly Leu Phe Thr Thr Gly Ala Lys Gln Asn Leu Tyr Leu Ile
            20                  25                  30
```

(2) INFORMATION FOR SEQ ID NO: 9:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 9:

```
Ser Thr Gln Val Thr Gly Gly Gln Ala Ala His Thr Val Arg Gly Val
1               5                   10                  15
Ala Ser Ile Phe Ser Pro Gly Ser Arg Gln Asp Ile Ser Leu Ile
            20                  25                  30
```

(2) INFORMATION FOR SEQ ID NO: 10:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 10:

```
Ser Thr Ile Val Ser Gly Gly Thr Val Ala Arg Thr Thr His Ser Leu
1               5                   10                  15
Ala Ser Leu Phe Thr Gln Gly Ala Ser Gln Lys Ile Gln Leu Ile
            20                  25                  30
```

(2) INFORMATION FOR SEQ ID NO: 11:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide

```
     (vi) ORIGINAL SOURCE:
          (A) ORGANISM: Hepatitis C Virus (xi) SEQUENCE DESCRIPTION: SEQ ID NO: 11:

Thr Ala Ser Arg Gln Ala Glu Val Ile Ala Pro Ala Val Gln Thr Asn
1               5                   10                  15

Trp Gln Lys Leu Glu Thr
            20

(2) INFORMATION FOR SEQ ID NO: 12:

(i) SEQUENCE CHARACTERISTICS:
         (A) LENGTH: 22 amino acids
         (B) TYPE: amino acid
         (C) STRANDEDNESS:
         (D) TOPOLOGY: linear (ii) MOLECULE TYPE: peptide (vi) ORIGINAL SOURCE:
          (A) ORGANISM: Hepatitis C Virus (xi) SEQUENCE DESCRIPTION: SEQ ID NO: 12:

Thr Ala Ser Arg His Ala Glu Val Ile Thr Pro Ala Val Gln Thr Asn
1               5                   10                  15

Trp Gln Lys Leu Glu Val
            20

(2) INFORMATION FOR SEQ ID NO: 13:

(i) SEQUENCE CHARACTERISTICS:
         (A) LENGTH: 22 amino acids
         (B) TYPE: amino acid
         (C) STRANDEDNESS:
         (D) TOPOLOGY: linear (ii) MOLECULE TYPE: peptide (vi) ORIGINAL SOURCE:
          (A) ORGANISM: Hepatitis C Virus (xi) SEQUENCE DESCRIPTION: SEQ ID NO: 13:

Thr Ala Thr Lys Gln Ala Glu Ala Ala Ala Pro Val Val Glu Ser Lys
1               5                   10                  15

Trp Arg Ala Leu Glu Val
            20

(2) INFORMATION FOR SEQ ID NO: 14:

(i) SEQUENCE CHARACTERISTICS:
         (A) LENGTH: 22 amino acids
         (B) TYPE: amino acid
         (C) STRANDEDNESS:
         (D) TOPOLOGY: linear (ii) MOLECULE TYPE: peptide (vi) ORIGINAL SOURCE:
          (A) ORGANISM: Hepatitis C Virus (xi) SEQUENCE DESCRIPTION: SEQ ID NO: 14:

Gln Ala Ser Lys Gln Ala Gln Asp Ile Gln Pro Ala Val Gln Ala Ser
1               5                   10                  15

Trp Pro Lys Val Glu Gln
            20
```

(2) INFORMATION FOR SEQ ID NO: 15:

(i) SEQUENCE CHARACTERISTICS:
       (A) LENGTH: 22 amino acids
       (B) TYPE: amino acid
       (C) STRANDEDNESS:
       (D) TOPOLOGY: linear (ii) MOLECULE TYPE: peptide (vi) ORIGINAL SOURCE:
       (A) ORGANISM: Hepatitis C Virus (xi) SEQUENCE DESCRIPTION: SEQ ID NO: 15:

Gln Ala Thr Arg Gln Ala Gln Asp Ile Gln Pro Ala Ile Gln Ser Ser
1               5                   10                  15

Trp Pro Lys Leu Glu Gln
            20

(2) INFORMATION FOR SEQ ID NO: 16:

(i) SEQUENCE CHARACTERISTICS:
       (A) LENGTH: 22 amino acids
       (B) TYPE: amino acid
       (C) STRANDEDNESS:
       (D) TOPOLOGY: linear (ii) MOLECULE TYPE: peptide (vi) ORIGINAL SOURCE:
       (A) ORGANISM: Hepatitis C Virus (xi) SEQUENCE DESCRIPTION: SEQ ID NO: 16:

Thr Ala Thr Lys Gln Ala Glu Ala Ala Pro Val Val Glu Ser Lys
1               5                   10                  15

Trp Arg Thr Leu Glu Ala
            20

(2) INFORMATION FOR SEQ ID NO: 17:

(i) SEQUENCE CHARACTERISTICS:
       (A) LENGTH: 20 amino acids
       (B) TYPE: amino acid
       (C) STRANDEDNESS:
       (D) TOPOLOGY: linear (ii) MOLECULE TYPE: peptide (vi) ORIGINAL SOURCE:
       (A) ORGANISM: Hepatitis C Virus (xi) SEQUENCE DESCRIPTION: SEQ ID NO: 17:

Ala Asn His Asp Ser Pro Asp Ala Glu Leu Ile Glu Ala Asn Leu Leu
1               5                   10                  15

Trp Arg Gln Glu
            20

(2) INFORMATION FOR SEQ ID NO: 18:

(i) SEQUENCE CHARACTERISTICS:
       (A) LENGTH: 20 amino acids
       (B) TYPE: amino acid
       (C) STRANDEDNESS:
       (D) TOPOLOGY: linear (ii) MOLECULE TYPE: peptide (vi) ORIGINAL SOURCE:
       (A) ORGANISM: Hepatitis C Virus (xi) SEQUENCE DESCRIPTION: SEQ ID NO: 18:

Thr His His Asp Ser Pro Asp Ala Asp Leu Ile Glu Ala Asn Leu Leu
1               5                   10                  15

Trp Arg Gln Glu
            20

(2) INFORMATION FOR SEQ ID NO: 19:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 19:

Thr His His Val Ser Pro Asp Ala Asp Leu Ile Glu Ala Asn Leu Leu
1               5                   10                  15

Trp Arg Gln Glu
            20

(2) INFORMATION FOR SEQ ID NO: 20:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 20:

Thr His Gly Lys Ala Tyr Asp Val Asp Met Val Asp Ala Asn Leu Phe
1               5                   10                  15

(2) INFORMATION FOR SEQ ID NO: 21:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 21:

Thr His Lys Thr Ala Tyr Asp Cys Asp Met Val Asp Ala Asn Leu Phe
1               5                   10                  15

(2) INFORMATION FOR SEQ ID NO: 22:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (vi) ORIGINAL SOURCE:
            (A) ORGANISM: Hepatitis C Virus (xi) SEQUENCE DESCRIPTION: SEQ ID NO: 22:

Thr Arg His Thr Pro Pro Asp Ala Asp Leu Ile Glu Ala Asn Leu Leu
1               5                   10                  15

Trp Arg Gln Glu
            20

(2) INFORMATION FOR SEQ ID NO: 23:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 23:

Pro Glu Gln Val Glu Leu Gln Pro Pro Gln Gly Gly Val Val Thr
1               5                   10                  15

Pro Gly (2) INFORMATION FOR SEQ ID NO: 24:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 24:

Phe Glu Pro Val Gly Ser Ala Pro Pro Ser Glu Gly Glu Cys Glu Val
1               5                   10                  15

Ile Asp (2) INFORMATION FOR SEQ ID NO: 25:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 25:

Ala Glu Leu Ala Thr Arg Ser Phe Gly
1               5

(2) INFORMATION FOR SEQ ID NO: 26:

(i) SEQUENCE CHARACTERISTICS:
        (A) LENGTH: 9 amino acids
        (B) TYPE: amino acid
        (C) STRANDEDNESS:

(D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 26:

Ala Glu Leu Ala Thr Lys Ser Phe Gly
1               5

(2) INFORMATION FOR SEQ ID NO: 27:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 27:

Ala Glu Leu Ala Thr Lys Thr Phe Gly
1               5

(2) INFORMATION FOR SEQ ID NO: 28:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 28:

Gln Gln Leu Ala Ile Lys Ser Phe Gly Gln Pro Pro Pro
1               5                   10

(2) INFORMATION FOR SEQ ID NO: 29:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Hepatitis C Virus (xi) SEQUENCE DESCRIPTION: SEQ ID NO: 29:

Arg Glu Met Ala Asp Lys Val Leu Ser Pro Leu Gln Asp
1               5                   10

(2) INFORMATION FOR SEQ ID NO: 30:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (vi) ORIGINAL SOURCE:
             (A) ORGANISM: Hepatitis C Virus (xi) SEQUENCE DESCRIPTION: SEQ ID NO: 30:

Ala Glu Leu Ala Thr Lys Thr Phe Gly
1               5

(2) INFORMATION FOR SEQ ID NO: 31:

(i) SEQUENCE CHARACTERISTICS:
             (A) LENGTH: 18 amino acids
             (B) TYPE: amino acid
             (C) STRANDEDNESS:
             (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /note= "A biotin group is attached
                 to Pro of position 1."

(ix) FEATURE:
             (A) NAME/KEY: Modified-site
             (B) LOCATION: 18
             (D) OTHER INFORMATION: /note= "A NH2 group is attached to
                 Tyr at position 18."

(xi) SEQUENCE DESCRIPTION: SEQ ID NO: 31:

Pro Ile Pro Lys Ala Arg Arg Pro Glu Gly Arg Thr Trp Ala Gln Pro
1               5                   10                  15

Gly Tyr (2) INFORMATION FOR SEQ ID NO: 32:

(i) SEQUENCE CHARACTERISTICS:
             (A) LENGTH: 18 amino acids
             (B) TYPE: amino acid
             (C) STRANDEDNESS:
             (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /note= "A biotin group is attached
                 to Pro of position 1."

(ix) FEATURE:
             (A) NAME/KEY: Modified-site
             (B) LOCATION: 18
             (D) OTHER INFORMATION: /note= "A NH2 group is attached to
                 Tyr at position 18."

(xi) SEQUENCE DESCRIPTION: SEQ ID NO: 32:

Pro Ile Pro Lys Asp Arg Arg Ser Thr Gly Lys Ser Trp Gly Lys Pro
1               5                   10                  15

Gly Tyr (2) INFORMATION FOR SEQ ID NO: 33:

(i) SEQUENCE CHARACTERISTICS:
             (A) LENGTH: 21 amino acids
             (B) TYPE: amino acid
             (C) STRANDEDNESS:
             (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /note= "A biotin group is attached
                   to Ala of position 1."

(ix) FEATURE:
              (A) NAME/KEY: Modified-site
              (B) LOCATION: 21
              (D) OTHER INFORMATION: /note= "A NH2 group is attached to
                   Gly at position 21."

(xi) SEQUENCE DESCRIPTION: SEQ ID NO: 33:

Ala Thr Arg Asp Gly Lys Leu Pro Ala Thr Gln Leu Arg Arg His Ile
1               5                   10                  15

Asp Leu Leu Lys Gly
            20

(2) INFORMATION FOR SEQ ID NO: 34:

(i) SEQUENCE CHARACTERISTICS:
              (A) LENGTH: 21 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /note= "A biotin group is attached
                   to Ala of position 1."

(ix) FEATURE:
              (A) NAME/KEY: Modified-site
              (B) LOCATION: 21
              (D) OTHER INFORMATION: /note= "A NH2 group is attached to
                   Gly at position 21."

(xi) SEQUENCE DESCRIPTION: SEQ ID NO: 34:

Ala Ala Arg Asn Ser Ser Ile Pro Thr Thr Thr Ile Arg Arg His Val
1               5                   10                  15

Asp Leu Leu Val Gly
            20

(2) INFORMATION FOR SEQ ID NO: 35:

(i) SEQUENCE CHARACTERISTICS:
              (A) LENGTH: 21 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /note= "A biotin group is attached
                   to Ala of position 1."

(ix) FEATURE:
              (A) NAME/KEY: Modified-site
              (B) LOCATION: 21
              (D) OTHER INFORMATION: /note= "A NH2 group is attached to
                   Met at position 21."

(xi) SEQUENCE DESCRIPTION: SEQ ID NO: 35:

Ala Val Gln Gln Pro Gly Ala Leu Thr Gln Gly Leu Arg Thr His Ile
1               5                   10                  15

```
Asp Met Val Val Met
            20

(2) INFORMATION FOR SEQ ID NO: 36:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "A biotin group is attached
             to Ala of position 1."

(ix) FEATURE:
        (A) NAME/KEY: Modified-site
        (B) LOCATION: 21
        (D) OTHER INFORMATION: /note= "A NH2 group is attached to
             Met at position 21."

(xi) SEQUENCE DESCRIPTION: SEQ ID NO: 36:

Ala Val Lys His Arg Gly Ala Leu Thr Arg Ser Leu Arg Thr His Val
1               5                   10                  15

Asp Met Ile Val Met
            20

(2) INFORMATION FOR SEQ ID NO: 37:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "A biotin group is attached
             to Ser of position 1."

(ix) FEATURE:
        (A) NAME/KEY: Modified-site
        (B) LOCATION: 9
        (D) OTHER INFORMATION: /note= "A NH2 group is attached to
             Gln at position 9."

(xi) SEQUENCE DESCRIPTION: SEQ ID NO: 37:

Ser Gln His Leu Pro Tyr Ile Glu Gln
1               5

(2) INFORMATION FOR SEQ ID NO: 38:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "A biotin group is attached
             to Ala of position 1."
```

(ix) FEATURE:
            (A) NAME/KEY: Modified-site
            (B) LOCATION: 9
            (D) OTHER INFORMATION: /note= "A NH2 group is attached to
                Gln at position 9."

(xi) SEQUENCE DESCRIPTION: SEQ ID NO: 38:

Ala Ser His Leu Pro Tyr Ile Glu Gln
1               5

(2) INFORMATION FOR SEQ ID NO: 39:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "A biotin group is attached
                to Ala of position 1."

(ix) FEATURE:
            (A) NAME/KEY: Modified-site
            (B) LOCATION: 9
            (D) OTHER INFORMATION: /note= "A NH2 group is attached to
                Glu at position 9."

(xi) SEQUENCE DESCRIPTION: SEQ ID NO: 39:

Ala Ser Arg Ala Ala Leu Ile Glu Glu
1               5

(2) INFORMATION FOR SEQ ID NO: 40:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "A biotin group is attached
                to Ala of position 1."

(ix) FEATURE:
            (A) NAME/KEY: Modified-site
            (B) LOCATION: 9
            (D) OTHER INFORMATION: /note= "A NH2 group is attached to
                Glu at position 9."

(xi) SEQUENCE DESCRIPTION: SEQ ID NO:40:

Ala Ser Lys Ala Ala Leu Ile Glu Glu
1               5

(2) INFORMATION FOR SEQ ID NO: 41:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide

```
    (ix) FEATURE:
         (A) NAME/KEY: Modified-site
         (B) LOCATION: 1
         (D) OTHER INFORMATION: /note= "A biotin group is attached
             to Gln of position 1."

(ix) FEATURE:
         (A) NAME/KEY: Modified-site
         (B) LOCATION: 9
         (D) OTHER INFORMATION: /note= "A NH2 group is attached to
             Thr at position 9."

(xi) SEQUENCE DESCRIPTION: SEQ ID NO:41:

Gln Lys Ala Leu Gly Leu Leu Gln Thr
1               5

(2) INFORMATION FOR SEQ ID NO: 42:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "A biotin group is attached
             to Ser of position 1."

(ix) FEATURE:
         (A) NAME/KEY: Modified-site
         (B) LOCATION: 9
         (D) OTHER INFORMATION: /note= "A NH2 group is attached to
             Gln at position 9."

(xi) SEQUENCE DESCRIPTION: SEQ ID NO:42:

Ser Lys Ile Gln Gly Leu Leu Gln Gln
    1               5

(2) INFORMATION FOR SEQ ID NO: 43:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "A biotin group is attached
             to Ser of position 1."

(ix) FEATURE:
         (A) NAME/KEY: Modified-site
         (B) LOCATION: 15
         (D) OTHER INFORMATION: /note= "A NH2 group is attached to
             Asp at position 15."

(xi) SEQUENCE DESCRIPTION: SEQ ID NO:43:

Ser Arg Arg Phe Ala Gln Ala Leu Pro Val Trp Ala Arg Pro Asp
1               5                   10                  15

(2) INFORMATION FOR SEQ ID NO: 44:

(i) SEQUENCE CHARACTERISTICS:
        (A) LENGTH: 15 amino acids
        (B) TYPE: amino acid
```

```
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "A biotin group is attached
             to Pro of position 1."

(ix) FEATURE:
         (A) NAME/KEY: Modified-site
         (B) LOCATION: 15
         (D) OTHER INFORMATION: /note= "A NH2 group is attached to
             Asp at position 15."

(xi) SEQUENCE DESCRIPTION: SEQ ID NO:44:

Pro Arg Lys Phe Pro Pro Ala Leu Pro Ile Trp Ala Arg Pro Asp
1               5                   10                  15

(2) INFORMATION FOR SEQ ID NO: 45:

(i) SEQUENCE CHARACTERISTICS:
         (A) LENGTH: 15 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "A biotin group is attached
             to Lys of position 1."

(ix) FEATURE:
         (A) NAME/KEY: Modified-site
         (B) LOCATION: 15
         (D) OTHER INFORMATION: /note= "A NH2 group is attached to
             Asp at position 15."

(xi) SEQUENCE DESCRIPTION: SEQ ID NO:45:

Lys Lys Arg Phe Pro Pro Ala Leu Pro Ala Trp Ala Arg Pro Asp
1               5                   10                  15

(2) INFORMATION FOR SEQ ID NO: 46:

(i) SEQUENCE CHARACTERISTICS:
         (A) LENGTH: 15 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "A biotin group is attached
             to Arg of position 1."

(ix) FEATURE:
         (A) NAME/KEY: Modified-site
         (B) LOCATION: 15
         (D) OTHER INFORMATION: /note= "A NH2 group is attached to
             Asp at position 15."

(xi) SEQUENCE DESCRIPTION: SEQ ID NO:46:

Arg Arg Lys Phe Pro Pro Ala Leu Pro Pro Trp Ala Arg Pro Asp
1               5                   10                  15
```